US010080553B2

United States Patent
Knodel et al.

(10) Patent No.: US 10,080,553 B2
(45) Date of Patent: Sep. 25, 2018

(54) MEDICAL INSTRUMENT

(71) Applicant: Richard Wolf GmbH, Knittlingen (DE)

(72) Inventors: Frank Knodel, Knittlingen (DE);
Eberhard Körner, Knittlingen (DE);
Markus Lienhart, Ottersweier (DE)

(73) Assignee: Richard Wolf GmbH, Knittlingen (DE)

( * ) Notice: Subject to any disclaimer, the term of this patent is extended or adjusted under 35 U.S.C. 154(b) by 519 days.

(21) Appl. No.: 14/661,149

(22) Filed: Mar. 18, 2015

(65) Prior Publication Data
US 2015/0265260 A1   Sep. 24, 2015

(30) Foreign Application Priority Data

Mar. 19, 2014   (DE) .................. 10 2014 205 080

(51) Int. Cl.
*A61B 17/00* (2006.01)
*A61B 1/00* (2006.01)
*A61B 17/34* (2006.01)

(52) U.S. Cl.
CPC .......... *A61B 17/00* (2013.01); *A61B 1/00128* (2013.01); *A61B 17/3421* (2013.01); *A61B 2017/00477* (2013.01); *A61B 2017/347* (2013.01)

(58) Field of Classification Search
CPC ............... A61B 19/22; A61B 19/2203; A61B 2019/2242; A61B 17/00; A61B 1/00128; A61B 17/3421
USPC .......................................................... 606/1
See application file for complete search history.

(56) References Cited

U.S. PATENT DOCUMENTS

| 5,171,245 | A |   | 12/1992 | Cezana |            |
|-----------|---|---|---------|--------|------------|
| 5,307,804 | A | * | 5/1994  | Bonnet | A61B 1/042 |
|           |   |   |         |        | 396/17     |
| 6,102,910 | A | * | 8/2000  | Boebel | A61B 18/1442 |
|           |   |   |         |        | 606/205    |
| 2005/0125027 | A1 | * | 6/2005 | Knodel | A61B 17/29 |
|           |   |   |         |        | 606/205    |

(Continued)

FOREIGN PATENT DOCUMENTS

DE          41 05 326 A1   9/1992
DE   10 2006 010 316 A1   9/2007

*Primary Examiner* — Daniel Cerioni
(74) *Attorney, Agent, or Firm* — McGlew and Tuttle, P.C.

(57) ABSTRACT

A medical instrument includes instrument parts which can be releasably connected to one another. One part includes a hollow-cone-shaped receiving space and another part includes a cone-shaped coupling section which can be inserted into the receiving space to connect the parts. The coupling section includes a locking receiver for a locking element of the receiving space and which can be brought into and out of engagement with the locking receiver. A securing element moves between a position holding the locking element in a locking position, and a position releasing the locking element. An actuation element projects into the receiving space of the first instrument part, engages into the locking receiver in the locking position of the locking element and is movable in the direction of its middle axis. The middle axis of the actuation element is aligned in the proximal direction obliquely to a middle axis of the receiving space.

23 Claims, 2 Drawing Sheets

(56) References Cited

U.S. PATENT DOCUMENTS

| | | | |
|---|---|---|---|
| 2006/0009677 A1* | 1/2006 | Lehmann | A61B 1/00126 600/104 |
| 2009/0198343 A1* | 8/2009 | Spain | A61F 2/30767 623/23.53 |
| 2014/0066709 A1* | 3/2014 | Mirza | A61B 17/32002 600/106 |

* cited by examiner

MEDICAL INSTRUMENT

CROSS REFERENCE TO RELATED APPLICATIONS

This application claims the benefit of priority under 35 U.S.C. § 119 of German Patent Application DE 10 2014 205 080.4 filed Mar. 19, 2014, the entire contents of which are incorporated herein by reference.

FIELD OF THE INVENTION

The invention relates to a medical instrument.

BACKGROUND OF THE INVENTION

With medical instruments, there often exists the need to releasably connect instrument parts to one another in a gas-tight and fluid-tight manner. One example of this is endoscopic shank instruments, with which an exchangeable working insert which is led through the shank of the instrument is fixed at the proximal end of the shank in a gas-tight or fluid-tight manner.

Cone connections, which are secured from unintended release by way of positive-fit means, are particularly suitable for creating a gas-tight or fluid-tight connection of such instrument parts. In this context, it is known to lock the cone connection by way of a bayonet closure, wherein an end section of a second instrument part which corresponds to the receiving space of the first instrument part is inserted into this conically designed receiving space, and the two instrument parts are positively and non-positively connected to one another with an externally attached clamping ring forming part of the bayonet closure. The creation of the connection of the two instrument parts is comparatively uncomfortable since the clamping ring must be brought into a prescribed position by way of a suitable rotation, before the connection of the two instrument parts as well as for the release of the connection.

SUMMARY OF THE INVENTION

Against this background, it is an object of the invention, to create a medical instrument, with which two instrument parts can be connected to one another in a quick and uncomplicated manner and in a further development of the invention can be separated from one another just as quickly and simply.

The medical instrument according to the invention comprises at least two instrument parts which are releasably connectable to one another. A first instrument part is provided with a hollow-cone-shaped receiving space, whereas a second instrument part comprises a cone-shaped coupling section which can be inserted into the receiving space of the first instrument part, for connecting these two instrument parts. The conicities of the receiving space formed on the first instrument part and of the coupling section formed on the second instrument part preferably correspond, so that an at least fluid-tight and preferably gas-tight contact or connection of the first and second instrument part arises.

The coupling section of the second instrument part comprises at least one locking receiver for a locking element which is arranged on the first instrument part and can be engaged with and disengaged from the locking receiver. With regard to the locking receiver, it is preferably the case of a recess or deepening, which is formed on the outer side of the coupling section of the second instrument part and which in the introduction direction of the coupling part into the receiving space, is distanced to the end of the coupling section which can be introduced into the receiving space of the first instrument head. The locking element which is preferably formed by a pin, usefully in the region of the receiving space of the first instrument part, is movably arranged relative to the second instrument part in a manner such that it can be engaged with the locking receiver formed on the coupling part of the second instrument part, for the positive connection of both instrument parts, and can be disengaged again for separating the two instrument parts. For this, the locking element usefully engages into the receiving space of the first instrument part. A securing element is provided, in order to be able to fix the locking element in its position engaging into the locking receiver. This element is movable between a first position, in which it holds the locking element in the locking position, and a second position, in which is releases the locking element.

According to the invention, the securing element is coupled in movement to an actuation element which projects into the receiving space of the first instrument part and in the locking position of the locking element engages into the locking receiver of the second instrument part. This actuation element which is preferably designed in a pin-like manner is movable in the direction of its middle axis which is aligned in the proximal direction obliquely to a middle axis of the receiving space. I.e., the middle axis of the actuation element runs obliquely to the introduction direction of the coupling section of the second instrument part into the receiving space of the first instrument part. The middle axis of the actuation element is advantageously aligned at an angle between 45° to maximal 90° and preferably an angle of 55° obliquely to the middle axis of the receiving space.

If the coupling section of the second instrument part is introduced into the receiving space of the first instrument part, then the coupling section with its outer side contacts the end of the actuation element which projects into the receiving space of the first instrument part and on account of the alignment of the actuation element obliquely to the introduction direction of the coupling part and on account of the cone-shaped design of the coupling part moves this actuation element out of the receiving space of the first instrument part. The securing element which is coupled in movement to the actuation element is moved by way of this movement of the actuation element from its first position into its second position, in which it releases the locking element. The end of the locking element which projects into the receiving space of the first instrument part, on account of this can firstly be forced out of the receiving space by the coupling section of the second instrument part. With a further movement of the coupling section of the second instrument part into the receiving space of the first instrument part, the actuation element engages into a recess which is formed on the outer side of the coupling section of the second instrument part and with which recess it is preferably the case of a locking receiver. The securing element by way of this can move back again into its first position, in which it pressure-impinges the locking element in the direction of the coupling section of the second instrument part, and when the locking receiver formed on the coupling section of the second instrument part is located directly in front of the locking element, then presses it into the locking receiver and holds it in this locking position. Accordingly, with the medical instrument according to the invention, a secure connection of its first instrument part to its second instrument part can be created in a rapid and simpler manner solely by way of the introduction of the coupling section of the second instrument part into the receiving space of the first instrument part. With a suitable material selection of the locking element and of the coupling section of the second instrument part, for example if the locking instrument and the coupling section are designed of a metallic material, then the user of the instrument according to the invention hears a detent noise which notifies him of a secure connection of the two instrument parts of the instrument.

The locking receiver formed on the coupling section of the second instrument part preferably runs over the whole outer periphery of the coupling section. Preferably, a groove extending over the whole outer periphery of the coupling section is accordingly formed on the outer lateral surface of the coupling section. This design measure has the advantage that the first and the second instrument part can be connected to one another independently of a relative rotational position, since the locking element and the actuation element can engage into the locking receiver formed on the coupling section of the second instrument part, independently of this rotation position. The connection of the two instrument parts is further simplified due to this.

The locking receiver further preferably has a trapezoidal cross section. Thus, one preferably envisages the width of a groove which extends around the outer periphery of the coupling section of the second instrument part and which forms the locking receiver continuously reducing in the radial direction of the coupling section, and the groove accordingly being delimited by two side walls which lie opposite one another and which taper to one another in an oblique manner in the radial direction of the coupling section.

A trapezoidal cross section of the locking receiver is particularly advantageous if, as is envisaged according to a further preferred design, an end section of the locking element which engages into the locking receiver is designed in a truncated-cone-like manner. The gradient of the end section of the locking element which is designed in a truncated-cone-like manner and at least the gradient of the side wall of the locking receiver which is at the front in the introduction direction of the second instrument part hereby usefully correspond to one another, so that the end section which is designed in truncated-cone-like manner bears on this side wall in a surfaced (flat) manner in the locking position of the locking element in the locking receiver. This measure permits an adequate self-locking of the locking element in the locking receiver and moreover reduces the proneness of the locking receiver and/or of the locking element to wear, on separating the second instrument part from the first instrument part, i.e. on withdrawing the coupling section of the second instrument part from the receiving space of the first instrument part.

A through-hole which is aligned transversely to the connection direction of the first and second instrument part is advantageously formed on the first instrument part for the movable arrangement of the locking element on this first instrument part. The locking element usefully extends through the through-hole and runs out in the receiving space. Hereby, the locking element is advantageously dimensioned such that its projects on an outer side which is away from the receiving space of the first instrument part, when the locking element is located in its locking position.

The securing element which holds the locking element in a first position in its locking position and releases it in a second position, is preferably formed by a sleeve which is displaceably arranged on the outer side of the first instrument part in the connection direction of the two instrument parts. Accordingly, the securing element or the sleeve forming the securing element is displaceable from its first position into its second position, and vice versa, in the axial direction of the receiving space. The securing element is usefully arranged in a region on the outer side of the receiving space which is formed on the first instrument part.

In one advantageous further development of the securing element, a contact surface for the locking element, i.e. for its end projecting outwards at the outer side on the first instrument part, and which is aligned a obliquely to the movement direction of the locking element is formed inner side of the securing element. This obliquely aligned contact surface of the securing element is usefully designed such that the locking element is pushed by the securing element in to its locking position, in the first position of the securing element, wherein the distance of the contact surface of the securing element to the end of the locking element which projects out of the first instrument part at the outer side increases with a movement of the securing element into its second position, so that a continuously increasing free space results between the outer side of the first instrument part and the securing element which is arranged around this, into which free space the locking element can retreat or move back on separating the second instrument part from the first instrument part, and is then no longer engages with the locking receiver formed on the coupling section of the second instrument part.

As has been already noted, the actuation element projecting into the receiving space of the first instrument part moves out of the receiving space, and the securing element which is coupled in movement thereto is moved from its first position into its second position, in which it releases the locking element, on introducing the coupling section of the second instrument part into the receiving space of the first instrument part. The securing element must be moved back into its first position again as soon as the coupling section of the second instrument part is inserted so far into the receiving space of the first instrument part that the actuation element and the locking element can engage into the locking receiver formed on the coupling section of the second instrument part, by which means the actuation element and the locking element are pressed into the locking receiver. In this context, it is particularly advantageous if the securing element is moved automatically into its first position. The securing element is preferably actively connected to a spring element in a manner such that the securing element is moved into the first position by way of a spring force produced by the spring element, for this purpose.

Usefully, a through-hole is formed on the first instrument part for the movable arrangement of the actuation element on this first instrument part. This through-hole, due to the oblique alignment of the middle axis of the actuation element which is envisaged according to the invention, typically tapers counter to the connection direction of the two instrument parts, obliquely or at right angles to the middle axis of the receiving space.

The coupling of movement of the actuation element to the securing element, with the instrument according to the invention is preferably not effected via a fixed connection of the actuation element and securing element, but instead via a loose contact of these two elements. A contact surface aligned obliquely to the connection direction of the two instruments is advantageously formed on the inner side of the securing element, also for the actuation element for this. This obliquely aligned contact surface on the securing element leads to a force component which thus moves the securing element in the insertion direction of the second instrument part and acts in the movement direction of the securing element, acting upon the securing element when the actuation element is moved out of the receiving space on introducing the coupling part of the second instrument part into the receiving space of the first instrument part.

The securing element preferably has a contact surface for the locking element and which is designed in a bevelled manner, as well as a contact surface for the actuation element and which is designed in a bevelled manner. The contact surface for the locking element and the contact surface for the actuation element are usefully aligned at different angles to the connection direction of the two instrument parts. The purpose of this different angle of the two contact surfaces provided on the securing element is to control the movement procedure or point in time of engagement of the actuation element and locking element into the locking receiver formed on the coupling section of the second instrument part. The angles of the two contact surfaces which are formed on the securing element are usefully selected in a manner such that firstly the actuation element and thereafter the locking element engage into the locking receiver formed on the second instrument part.

The securing element must be manually moved into its second position, in which it releases the locking element, for separating the second instrument part from the first instrument part. Thus, the securing element is advantageously coupled in movement to the grip part, in order to simplify the handling of this securing element. The grip part can be a separate part which is fixedly connected to the securing element or it can form an integral component of the securing element. Usefully, the grip part is designed and arranged in a manner such that it can be actuated just as well by left-handed persons and right-handed persons, from each peripheral position of the first instrument part. Thus, the grip part can advantageously be designed in an annular manner wherein it is arranged on the outer lateral surface of the securing element.

An end region of the locking element and of the actuation element and contacting the coupling section of the second instrument part in each case is advantageously provided with a low-friction coating. Accordingly, the end region of the locking element which projects in the receiving space of the first instrument part, as well as the end region of the actuation element which projects in the receiving space are provided with a coating which improves the sliding characteristics of the locking element and of the actuation element on contact of the coupling section of the second instrument part. Wear is reduced and in the best case is prevented on account of this measure, at the coupling section of the second instrument part as well as at the locking element and the actuation element. Such materials as are applied in the construction of sliding bearings can e.g. be used as coating materials. It is to be noted that as the case may be, the actuation element and the locking element can be formed completely from a sliding-bearing-optimized material instead of a coating provided on the locking element and the actuation element.

One further advantageously envisages forming a contact surface to the coupling section of the second instrument part and which is bevelled in a manner such that its contacts the coupling section in a surfaced which is to say flat manner, on the end of the actuation element which projects into the interior of the first instrument part, as a further measure.

The invention is hereinafter explained in more detail by way of an embodiment example shown in the drawings. The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

BRIEF DESCRIPTION OF THE DRAWINGS

In the drawings, shown in a schematically simplified manner and in different scales in each case.

DESCRIPTION OF THE PREFERRED EMBODIMENTS

Figure 1:
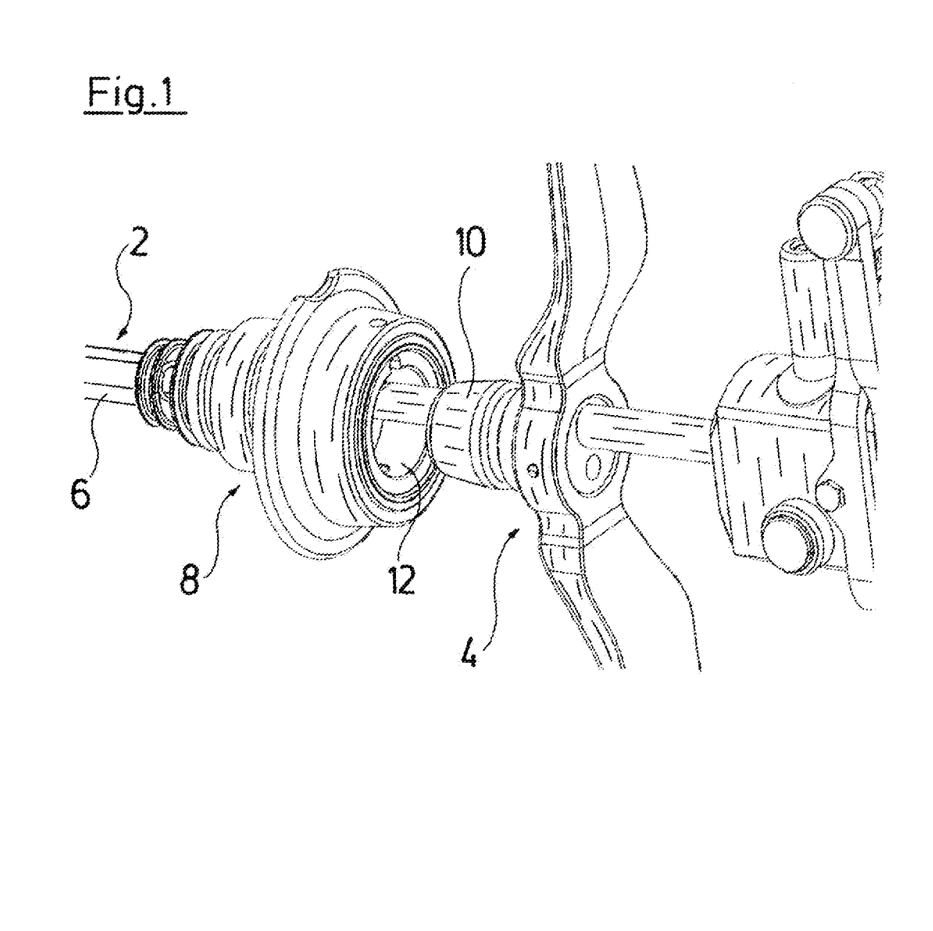
FIG. 1 in a perspective representation showing the connection region of a medical instrument with two instrument parts which are to be connected.

With the medical instrument represented in FIG. 1, it is the case of an endoscopic instrument with a first instrument part in the form of a hollow shank 2 which can be introduced into the inside of the body, and with a second instrument part in the form of a working insert 4 which can be inserted into the hollow shank 2 and is connectable to the hollow shank 2 in a gas-tight manner.

The hollow shank 2 is formed by a tube 6, at whose proximal end a coupling device 8 is arranged for fixing the working insert 4. For this, the working insert 4 comprises a coupling section 10 which is introduced into a receiving space 12 which is open to the proximal side and which is formed on the coupling device 8 of the hollow shank 2.

The coupling section 10 of the working insert 4 has a distal region 14 which tapers in a cone-shaped manner in the distal direction. A cylindrically designed region 16 of the coupling section 10, on which a groove with a trapezoidal cross section and extending over the entire periphery of the coupling section 10 is formed, connects to the proximal end of the region 14 of the coupling section 10. This groove forms a locking receiver 18, whose significance will be dealt with in a more detailed manner hereinafter.

In a manner corresponding to the shaping of the coupling section 10 of the working insert 4, the receiving space 12 formed on the coupling device 8 of the hollow shank 2, at the proximal side comprises a cylindrically designed region which distally merges into a conically tapering region. A through-hole 20 which extends from a radial outer side of the coupling device 8 transversely to a middle axis A of the hollow shank 2 to the receiving space 12 runs out at the cylindrical region of the receiving space 12. The through-hole 20 comprises a radial widening 22 adjacently to the outer side of the coupling device 8.

A locking element 24 is guided in an axially displaceable manner in the through-hole 20 and serves for positively fixing the coupling section 10 of the working insert 4 in the receiving space 12 of the coupling device 8 of the hollow shank 2. The locking element 24 is formed by a pin. This pin comprises a cylindrical base body which tapers in a truncated-cone-shaped manner in an end section projecting into the receiving space 12. A head which projects radially beyond the outer periphery of the base body is formed on the other end of the base body, wherein the outer diameter of the head corresponds to the inner diameter of the widening 22 formed on the through-hole 20. The head of the locking element 24 forms a contact shoulder which comes into contact on a shoulder formed by the widening 22 of the through-hole 20 and in this manner limits the movement path of the locking element 24. The locking element 24 is dimensioned such that it always projects out of the through-hole 20 at the end of this through hole which is away from the receiving space 12, independently of its displacement position.

A further through-hole 26 runs out at the cylindrical region of the receiving space 12, in a manner roughly diametrically opposite the through-hole 20. This through-hole 26 runs obliquely through the outer wall of the coupling device 8, wherein its middle axis B in the proximal direction is aligned at an angle obliquely to the middle axis A of the hollow shank 2 or of the receiving space 12. An actuation element 28 is axially displaceably guided in the through-hole 26 and the significance of this will be explained in more detail hereinafter.

The coupling device 8 in the region of the proximal end of this is surrounded by a component which forms a securing element 30 for the locking element 24. The securing element 30 is displaceable in the direction of the middle axis A on the coupling device 8, wherein it is secured against a rotation movement about the middle axis A by way of a keyway connection to the coupling device 8, which is not evident from the drawings.

The securing element 30 has an essentially sleeve-like base body, on which two tongues 32 and 34 extending in the distal direction are formed at the distal side. The tongues 32 and 34 are arranged in a manner such that the tongue 32 with its inner side facing the outer side of the coupling device 8 contacts the locking element 24, and the tongue 34 with its inner side facing the outer side of the coupling device 8 contacts the actuation element 28. The contact of the tongue 32 with the locking element 24 is effected via a contact surface 36 which is formed on the inner side of the tongue 32 and which is aligned obliquely to the middle axis A of the hollow shank 2 in a manner such that the radial distance of the securing element 30 to the outer side of the coupling device 8 increases in the proximal direction. The tongue 34 contacts the actuation element 28 via a contact surface 38 which is formed on the inner side of this tongue and which is likewise aligned obliquely to the middle axis A of the hollow shank 2. The obliqueness of the contact surface 38 is also such that the radial distance of the securing element 30 to the outer side of the coupling device 8 increases in the proximal direction.

The securing element 30 in the direction of the middle axis A of the hollow shank 2 is supported on a spring element 40 in the form of a helical spring. This spring element 40 is arranged between an annular shoulder 42 formed on the outer periphery of the coupling device 8 of the hollow shank 2 and a shoulder formed on the outer side of the securing element 30 at the transition of the conical base body to the tongues 32 and 34.

The securing element 30 is connected to the grip part 44. This grip part 44 is arranged peripherally around the securing element 30 and is designed in an essentially sleeve-like manner, wherein the grip part 44 comprises a radially outwardly projecting annular shoulder 46 at its proximal end, for an improved handling.

The connection of the working insert 4 to the hollow shank 2 with the endoscopic instrument represented in the drawings is effected as follows:

The spring element 40, before the working insert 4 is inserted into the hollow shank 2, presses the securing element 30 into a first position, in which the securing element 30 via its tongue 32 holds the locking element 24 in its locking position, in which the truncated-cone-shaped end section of the locking element 24 projects into the receiving space 12 formed on the coupling device 8 of the hollow shank 2. The actuation element 28 is simultaneously also pressed by the tongue 34 of the securing element 30 into a position, in which the end section of the actuation element 28 projects into the receiving space 12.

Figure 2:
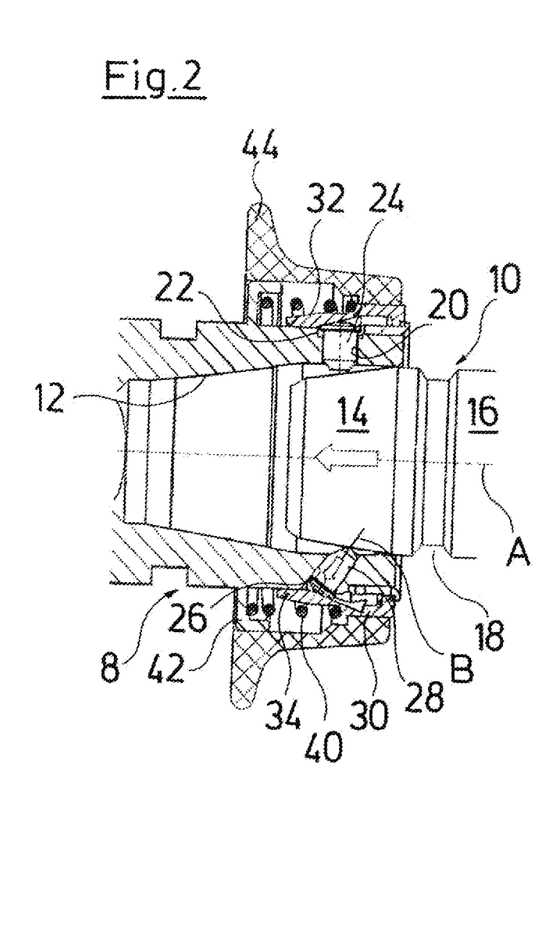
FIG. 2 is an enlarged sectioned view showing the connection region of the instrument according to FIG. 1, in the non-locked condition.
Figure 3:
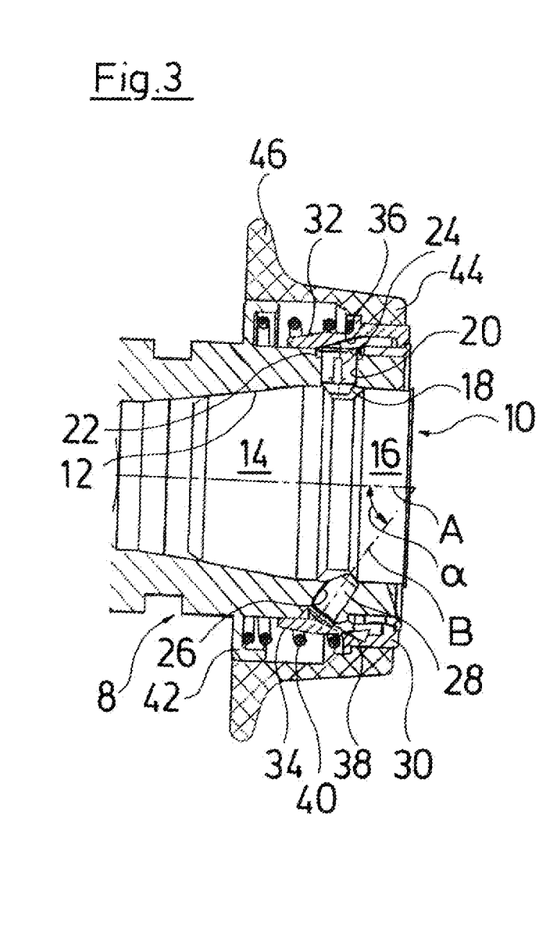
FIG. 3 is a representation according to FIG. 2, in the locked condition.

If, as is represented in FIG. 2, the working insert 4 is now inserted via the opening of the receiving space 12 into the hollow shank 2, then the region 14 of the coupling section 10 of the working insert 4 and which is formed in a cone-like manner comes into contact with a blunt tip which is formed at the end of the actuation element 28 which projects into the receiving space 12. The actuation element 28 is moved further in the direction out of the receiving space 12 with a further introduction movement of the working insert 4 in the distal direction. A force component acting in the direction of the middle axis A of the hollow shank 2 is exerted onto the securing element 30, due to the fact that the actuation element 28 contacts the bevelled contact surface 38 formed on the tongue 34 of the securing element 30, and this force component pushes the securing element 30 in the distal direction into its second position against the action of the spring element 40. The locking element 24 by way of this can firstly escape out of the receiving space 12 on contact with the region 14 of the coupling section 10 of the working insert 4, said region designed in a cone-like manner. As soon as the locking receiver 18 which is formed on the coupling section 10 is located directly in front of the end of the through-hole 26 which faces the receiving space 12, the actuation element 28 slips into the locking receiver 18, by which means the contact of the actuation element 28 with the securing element 30 is released, so that the spring element 40 moves the securing element 30 again in the direction of its first position. Hereby, the securing element 30 via the contact surface 36 formed on its tongue 32 pushes the locking element 24 into the locking receiver 18, in which the locking element 24 is held by the securing element 30 on reaching its second position.

The securing element 30, via the grip part 44 connected thereto is pushed in the distal direction against the effect of the spring element 40, for releasing the working insert 4 from the hollow shank 2. The locking element 24 and the actuation element 28 are released from the securing element 30 by way of this, so that the locking element 24 and the actuation element 28 can be pressed out of the receiving space 12 on withdrawing the coupling element 10 of the working insert 4 out of the receiving space 12 of the coupling device 8 of the hollow shank 2, and the working insert 4 can be separated from the hollow shank 2 without any problem.

While specific embodiments of the invention have been shown and described in detail to illustrate the application of the principles of the invention, it will be understood that the invention may be embodied otherwise without departing from such principles.

LIST OF REFERENCE NUMERALS

2 hollow shank
4 working insert
6 tube
8 coupling device
10 coupling section
12 receiving space
14 region
16 region 18 locking receiver
20 through-hole
22 widening
24 locking element
26 through-hole
28 actuation element
30 securing element
32 tongue
34 tongue
36 contact surface
38 contact surface
40 spring element
42 annular shoulder
44 grip part
46 annular shoulder
A middle axis
B middle axis
α angle

What is claimed is:

1. A medical instrument comprising:
a first instrument part comprising a hollow-cone-shaped receiving space and a locking element arranged on the first instrument part;
a second instrument part which can be releasably connected to the first instrument part, the second instrument part comprising a cone-shaped coupling section which can be inserted into the receiving space of the first instrument part, the coupling section comprising at least one locking receiver for the locking element which can be brought into and out of engagement with the locking receiver by movement into and out of a locking position;
a securing element movable between a first position, in which the securing element holds the locking element in the locking position, and a second position, in which the securing element releases the locking element; and
an actuation element coupled in movement to the securing element for moving the securing element from the first position to the second position, wherein:
the actuation element projects into the receiving space, engages into the locking receiver in the locking position of the locking element and is movable in a direction of a middle axis of the actuation element;
the middle axis of the actuation element is aligned in a proximal direction obliquely to a middle axis of the receiving space; and
the securing element is formed by a sleeve which is displaceably arranged on an outer side of the first instrument part in a connection direction of the first and second instrument parts.

2. A medical instrument according to claim 1, wherein the locking receiver, which is formed on the coupling section of the second instrument part, extends over a whole outer periphery of the coupling section.

3. A medical instrument according to claim 1, wherein the locking receiver has a trapezoidal cross section.

4. A medical instrument according to claim 1, wherein an end section of the locking element, which engages into the locking receiver, is formed in a shape of a truncated-cone.

5. A medical instrument according to claim 1, wherein:
a through-hole for a movable arrangement of the locking element is aligned transversely to a connection direction of the first and second instrument parts and extends out in the receiving space and is formed on the first instrument part; and
the locking element extends through the through-hole.

6. A medical instrument according to claim 1, wherein a contact surface for the locking element, which is aligned obliquely to a movement direction of the locking element, is formed on an inner side of the securing element.

7. A medical instrument according to claim 1, further comprising a spring element wherein the securing element is actively connected to the spring element in a manner such that the securing element is moved into the first position by a spring force produced by the spring element.

8. A medical instrument according to claim 1, wherein:
a through-hole for a movable arrangement of the actuation element is formed on the first instrument part;
the through-hole tapers obliquely or at right angles to a middle axis of the receiving space, counter to a connection direction of the two instrument parts.

9. A medical instrument according to claim 1, wherein a contact surface for the actuation element and aligned obliquely to the connection direction of the two instrument parts is formed on an inner side of the securing element.

10. A medical instrument according to claim 1, wherein:
a contact surface for the locking element, which is aligned obliquely to a movement direction of the locking element, is formed on an inner side of the securing element;
a contact surface for the actuation element and aligned obliquely to the connection direction of the two instrument parts is formed on an inner side of the securing element; and
the contact surface for the locking element and the contact surface for the actuation element are aligned at different angles to the connection direction of the two instrument parts.

11. A medical instrument according to claim 1, wherein:
a locking element through-hole for a movable arrangement of the locking element is aligned transversely to a connection direction of the first and second instrument parts and extends out in the receiving space and is formed on the first instrument part; and
the locking element extends through the locking element through-hole;
an actuation element through-hole for a movable arrangement of the actuation element is formed on the first instrument part;
the actuation element through-hole tapers obliquely or at right angles to a middle axis of the receiving space, counter to a connection direction of the two instrument parts; and
the locking element through-hole for the arrangement of the locking element and the actuation element through-hole for the arrangement of the actuation element are arranged in a manner such that an end section of the actuation element, which engages into the receiving space of the first instrument part, contacts the second instrument part, inserted into the receiving space, before an end section of the locking element engages into the receiving space.

12. A medical instrument according to claim 1, wherein the securing element is coupled to a grip part.

13. A medical instrument according to claim 1, wherein:
at least one end region of the locking element is provided with a locking element low-friction coating; and
at least one end region of the actuation element for contacting the coupling section of the second instrument part is provided with an actuation element low-friction coating.

14. A medical instrument according to claim 1, wherein a contact surface to the coupling section of the second instrument part is bevelled in a manner such that the contact surface contacts the coupling section in a flat manner and is formed on the end of the actuation element which projects into the receiving space of the first instrument part.

15. A medical instrument according to claim 1, wherein a middle axis of the actuation element is aligned at an angle between 45° to maximal 90° obliquely to the middle axis of the receiving space.

16. A medical instrument according to claim 1, wherein a middle axis of the actuation element is aligned at an angle of about 55° obliquely to the middle axis of the receiving space.

17. A medical instrument comprising:
a first instrument part comprising a hollow-cone-shaped receiving space and a locking element arranged on the first instrument part;
a second instrument part which can be releasably connected to the first instrument part, the second instrument part comprising a cone-shaped coupling section which can be inserted into the receiving space of the first instrument part, the coupling section comprising at least one locking receiver for the locking element which can be brought into and out of engagement with the locking receiver by movement into and out of a locking position;
a securing element movable between a first position, in which the securing element holds the locking element in the locking position, and a second position, in which the securing element releases the locking element; and
an actuation element coupled in movement to the securing element, wherein:
the actuation element projects into the receiving space, engages into the locking receiver in the locking position of the locking element and is movable in a direction of a middle axis of the actuation element;
the middle axis of the actuation element is aligned in a proximal direction obliquely to a middle axis of the receiving space; and
a contact surface for the locking element, which is aligned obliquely to a movement direction of the locking element, is formed on an inner side of the securing element.

18. A medical instrument comprising:
a first instrument part comprising a hollow-cone-shaped receiving space and a locking element arranged on the first instrument part;
a second instrument part which can be releasably connected to the first instrument part, the second instrument part comprising a cone-shaped coupling section which can be inserted into the receiving space of the first instrument part, the coupling section comprising at least one locking receiver for the locking element which can be brought into and out of engagement with the locking receiver by movement into and out of a locking position;
a securing element movable between a first position, in which the securing element holds the locking element in the locking position, and a second position, in which the securing element releases the locking element;
a spring element, wherein the securing element is actively connected to the spring element in a manner such that the securing element is moved into the first position by a spring force produced by the spring element; and
an actuation element coupled in movement to the securing element, wherein:
the actuation element projects into the receiving space, engages into the locking receiver in the locking position of the locking element and is movable in a direction of a middle axis of the actuation element; and
the middle axis of the actuation element is aligned in a proximal direction obliquely to a middle axis of the receiving space.

19. A medical instrument comprising:
a first instrument part comprising a hollow-cone-shaped receiving space and a locking element arranged on the first instrument part;
a second instrument part which can be releasably connected to the first instrument part, the second instrument part comprising a cone-shaped coupling section which can be inserted into the receiving space of the first instrument part, the coupling section comprising at least one locking receiver for the locking element which can be brought into and out of engagement with the locking receiver by movement into and out of a locking position;
a securing element movable between a first position, in which the securing element holds the locking element in the locking position, and a second position, in which the securing element releases the locking element; and
an actuation element coupled in movement to the securing element, wherein:
the actuation element projects into the receiving space, engages into the locking receiver in the locking position of the locking element and is movable in a direction of a middle axis of the actuation element;
the middle axis of the actuation element is aligned in a proximal direction obliquely to a middle axis of the receiving space;
a through-hole for a movable arrangement of the locking element is aligned transversely to a connection direction of the first and second instrument parts and extends out in the receiving space and is formed on the first instrument part; and
the locking element extends through the through-hole.

20. A medical instrument comprising:
a first instrument part comprising a hollow-cone-shaped receiving space and a locking element arranged on the first instrument part;
a second instrument part which can be releasably connected to the first instrument part, the second instrument part comprising a cone-shaped coupling section which can be inserted into the receiving space of the first instrument part, the coupling section comprising at least one locking receiver for the locking element which can be brought into and out of engagement with the locking receiver by movement into and out of a locking position;
a securing element movable between a first position, in which the securing element holds the locking element in the locking position, and a second position, in which the securing element releases the locking element; and
an actuation element coupled in movement to the securing element, wherein:
the actuation element projects into the receiving space, engages into the locking receiver in the locking position of the locking element and is movable in a direction of a middle axis of the actuation element;
the middle axis of the actuation element is aligned in a proximal direction obliquely to a middle axis of the receiving space;
a through-hole for a movable arrangement of the actuation element is formed on the first instrument part; and the through-hole tapers obliquely or at right angles to a middle axis of the receiving space, counter to a connection direction of the two instrument parts.

21. A medical instrument comprising:

a first instrument part comprising a hollow-cone-shaped receiving space and a locking element arranged on the first instrument part;

a second instrument part which can be releasably connected to the first instrument part, the second instrument part comprising a cone-shaped coupling section which can be inserted into the receiving space of the first instrument part, the coupling section comprising at least one locking receiver for the locking element which can be brought into and out of engagement with the locking receiver by movement into and out of a locking position;

a securing element movable between a first position, in which the securing element holds the locking element in the locking position, and a second position, in which the securing element releases the locking element; and an actuation element coupled in movement to the securing element, wherein:

the actuation element projects into the receiving space, engages into the locking receiver in the locking position of the locking element and is movable in a direction of a middle axis of the actuation element;

the middle axis of the actuation element is aligned in a proximal direction obliquely to a middle axis of the receiving space; and a contact surface for the actuation element and aligned obliquely to the connection direction of the two instrument parts is formed on an inner side of the securing element.

22. A medical instrument comprising:

a first instrument part comprising a hollow-cone-shaped receiving space and a locking element arranged on the first instrument part;

a second instrument part which can be releasably connected to the first instrument part, the second instrument part comprising a cone-shaped coupling section which can be inserted into the receiving space of the first instrument part, the coupling section comprising at least one locking receiver for the locking element which can be brought into and out of engagement with the locking receiver by movement into and out of a locking position;

a securing element movable between a first position, in which the securing element holds the locking element in the locking position, and a second position, in which the securing element releases the locking element; and an actuation element coupled in movement to the securing element, wherein:

the actuation element projects into the receiving space, engages into the locking receiver in the locking position of the locking element and is movable in a direction of a middle axis of the actuation element;

the middle axis of the actuation element is aligned in a proximal direction obliquely to a middle axis of the receiving space;

a contact surface for the locking element, which is aligned obliquely to a movement direction of the locking element, is formed on an inner side of the securing element; and a contact surface for the actuation element and aligned obliquely to the connection direction of the two instrument parts is formed on an inner side of the securing element; and the contact surface for the locking element and the contact surface for the actuation element are aligned at different angles to the connection direction of the two instrument parts.

23. A medical instrument comprising:

a first instrument part comprising a hollow-cone-shaped receiving space and a locking element arranged on the first instrument part;

a second instrument part which can be releasably connected to the first instrument part, the second instrument part comprising a cone-shaped coupling section which can be inserted into the receiving space of the first instrument part, the coupling section comprising at least one locking receiver for the locking element which can be brought into and out of engagement with the locking receiver by movement into and out of a locking position;

a securing element movable between a first position, in which the securing element holds the locking element in the locking position, and a second position, in which the securing element releases the locking element; and an actuation element coupled in movement to the securing element, wherein:

the actuation element projects into the receiving space, engages into the locking receiver in the locking position of the locking element and is movable in a direction of a middle axis of the actuation element;

the middle axis of the actuation element is aligned in a proximal direction obliquely to a middle axis of the receiving space;

a locking element through-hole for a movable arrangement of the locking element is aligned transversely to a connection direction of the first and second instrument parts and extends out in the receiving space and is formed on the first instrument part;

the locking element extends through the locking element through-hole;

an actuation element through-hole for a movable arrangement of the actuation element is formed on the first instrument part;

the actuation element through-hole tapers obliquely or at right angles to a middle axis of the receiving space, counter to a connection direction of the two instrument parts; and the locking element through-hole for the arrangement of the locking element and the actuation element through-hole for the arrangement of the actuation element are arranged in a manner such that an end section of the actuation element, which engages into the receiving space of the first instrument part, contacts the second instrument part, inserted into the receiving space, before an end section of the locking element engages into the receiving space.

* * * * *